(12) United States Patent
Porcs-Makkay et al.

(10) Patent No.: US 9,040,696 B2
(45) Date of Patent: May 26, 2015

(54) METHOD FOR PREPARING ROSUVASTATIN SALTS

(75) Inventors: Marta Porcs-Makkay, Pomaz (HU); Ferenc Lorant Bartha, Tiszavasvari (HU); Gyorgy Krasznai, Budapest (HU); Balazs Volk, Budapest (HU); Gyorgy Ruzsics, Budapest (HU); Laszlo Pongo, Kerepes (HU); Gyula Lukacs, Budapest (HU); Tibor Szabo, Budapest (HU); Jozsef Barkoczy, Budapest (HU); Jozsef Debreczeni, Budapest (HU); Adrienn Keszthelyi, Budapest (HU); Angela Pandur, Mende (HU); Eniko Molnar, Erd (HU); Matyas Milen, Budapest (HU); Maria Tothne Lauritz, Budapest (HU)

(73) Assignee: EGIS Gyogyszergyar Nyilvanosan Mukodo Reszvenytarsasag, Budapest (HU)

( * ) Notice: Subject to any disclaimer, the term of this patent is extended or adjusted under 35 U.S.C. 154(b) by 0 days.

(21) Appl. No.: 13/989,821

(22) PCT Filed: Nov. 29, 2011

(86) PCT No.: PCT/HU2011/000112
§ 371 (c)(1),
(2), (4) Date: Jul. 3, 2013

(87) PCT Pub. No.: WO2012/073054
PCT Pub. Date: Jun. 7, 2012

(65) Prior Publication Data
US 2013/0281694 A1    Oct. 24, 2013

(30) Foreign Application Priority Data
Nov. 29, 2010  (HU) .................................. 1000638

(51) Int. Cl.
*C07D 239/02* (2006.01)
*C07D 239/42* (2006.01)

(52) U.S. Cl.
CPC .................................. *C07D 239/42* (2013.01)

(58) Field of Classification Search
CPC ........................... C07D 239/28; C07D 239/42
See application file for complete search history.

(56) References Cited

U.S. PATENT DOCUMENTS

| 2009/0111839 A1 | 4/2009 | Zlicar et al. |
| 2009/0275752 A1 | 11/2009 | Reddy et al. |

FOREIGN PATENT DOCUMENTS

| WO | 2006136407 A1 | 12/2006 |
| WO | 2007125547 A2 | 11/2007 |
| WO | WO 2007125547 A2 * | 11/2007 |
| WO | 2010081861 A1 | 7/2010 |
| WO | WO 2010081861 A1 * | 7/2010 |
| WO | 2012073055 A1 | 6/2012 |

OTHER PUBLICATIONS

International Search Report from PCT/HU2011/000112 dated Sep. 12, 2012.

* cited by examiner

*Primary Examiner* — Noble Jarrell
*Assistant Examiner* — John S Kenyon
(74) *Attorney, Agent, or Firm* — Millen, White, Zelano, Branigan, P.C.

(57) ABSTRACT

The present invention is related to methods for the preparation of pharmaceutically acceptable salts of (+)-7-[4-(4-fluorophenyl)-6-isopropyl-2-(methanesulfonyl-methyl-amino)-pyrimidin-5-yl]-(3R,5S,6E)-dihydroxy-hept-6-enoic acid, intermediates thereof and methods for producing said intermediates.

22 Claims, 1 Drawing Sheet

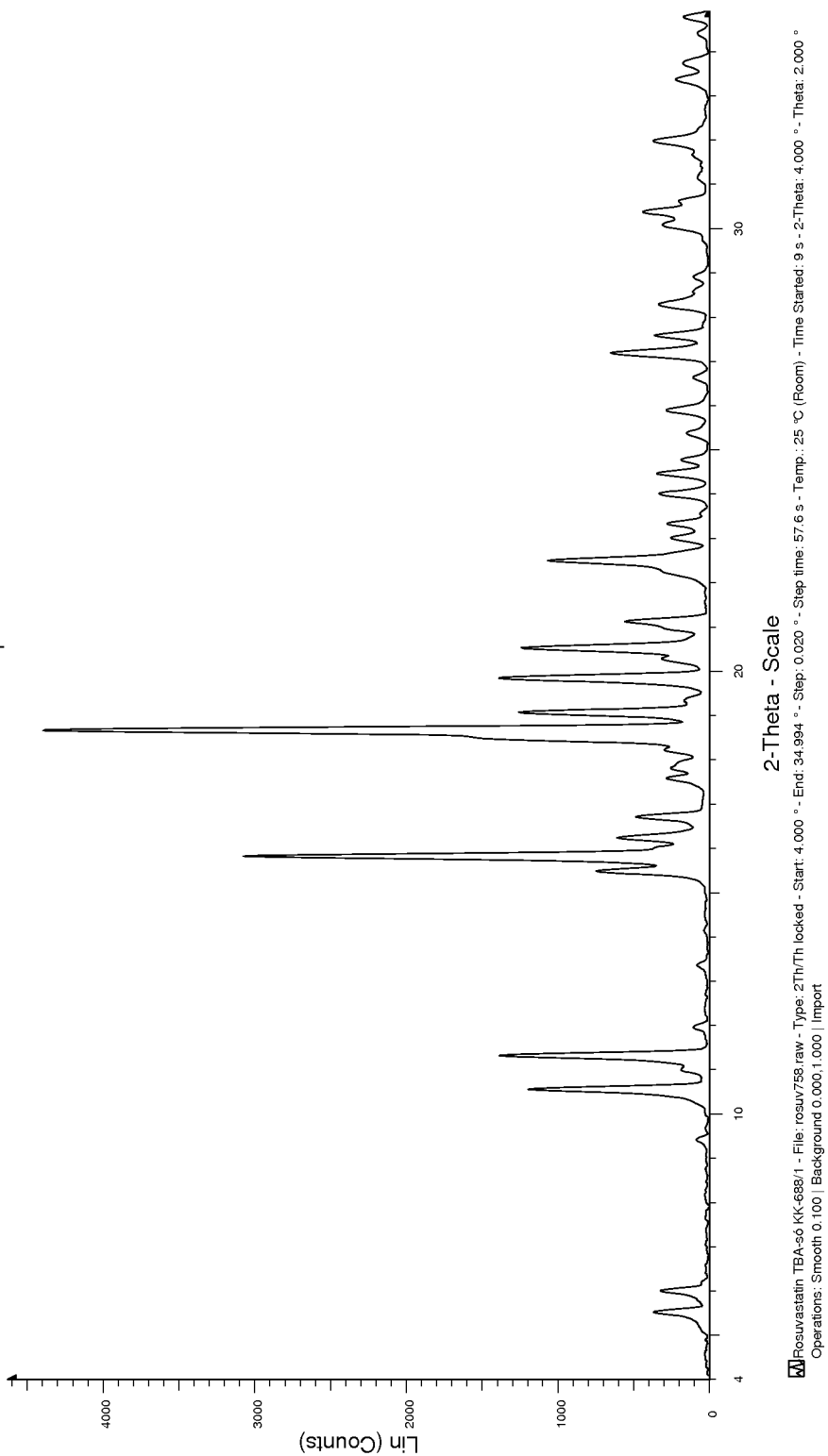

METHOD FOR PREPARING ROSUVASTATIN SALTS

TECHNICAL FIELD OF THE INVENTION

The present invention is related to methods for the preparation of pharmaceutically acceptable salts of (+)-7-[4-(4-fluorophenyl)-6-isopropyl-2-(methanesulfonyl-methyl-amino)-pyrimidin-5-yl]-(3R,5S,6E)-dihydroxy-hept-6-enoic acid, intermediates thereof and methods for producing said intermediates.

(+)-7-[4-(4-fluorophenyl)-6-isopropyl-2-(methanesulfonyl-methyl-amino)-pyrimidin-5-yl]-(3R,5S,6E)-dihydroxy-hept-6-enoic acid of the Formula (I)

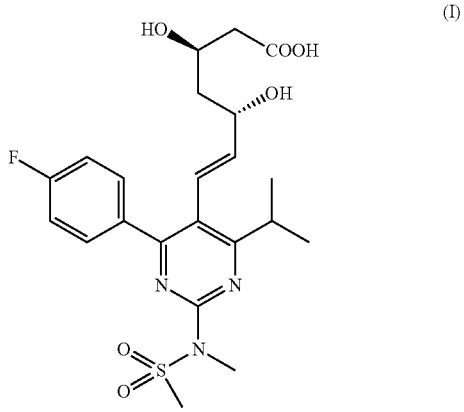 [SMILES: CC(C)c1nc(N(C)S(C)(=O)=O)nc(-c2ccc(F)cc2)c1/C=C/[C@@H](O)C[C@@H](O)CC(=O)O]

(I)

is a pharmaceutically active ingredient known by the International Nonproprietary Name rosuvastatin. Rosuvastatin exerts its pharmacological activity by inhibiting the enzyme 2-hydroxy-2-methyl-glutaryl-coenzyme-A reductase in the liver, thus decreasing the rate of the cholesterol biosynthesis and the cholesterol concentration of the blood plasma. Rosuvastatin of the Formula (I) is used in the therapy of diseases of lipid metabolism, such as hypercholesterolemia, hyperlipoproteinemia and atherosclerosis.

TECHNICAL BACKGROUND OF THE INVENTION (+)-7-[4-(4-fluorophenyl)-6-isopropyl-2-(methanesulfonyl-methyl-amino)-pyrimidin-5-yl]-(3R,5S)-dihydroxy-hept-6-enoic acid of the Formula (I) (rosuvastatin) is a compound known according the state of the art, which has been described for the first time in European Patent No. 521471 together with certain pharmaceutically acceptable salts including the ammonium salt and calcium salt of the Formula (IV)

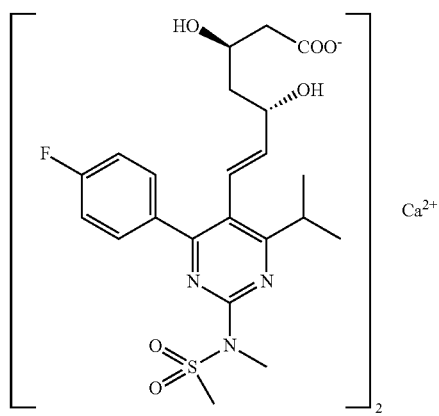

(IV)

Published International Patent Application WO01060804 discloses crystalline ammonium, methylammonium, ethylammonium, diethanolammonium, tris-(hydroxymethyl)-methylammonium, benzylammonium and 4-methoxybenzyl-ammonium salts of rosuvastatin. The method disclosed in said application for the preparation of the methylammonium salt comprises reacting rosuvastatin of the Formula (I) with methylamine in methanol, filtering and washing the filtered salt with acetonitrile. Other ammonium salts were prepared by acidifying the methylammonium salt in aqueous acetonitrile or water-ethylacetate biphasic solvent system and reacting rosuvastatin acid thus obtained with the corresponding amine.

The subject of Published International Patent Application WO2005051921 is a multi-step method for purifying rosuvastatin calcium salt of the Formula (IV) using rosuvastatin isopropylammonium or cyclohexylammonium salts. Rosuvastatin calcium salt of the Formula (IV) is acidified in aqueous acetonitrile solvent and rosuvastatin of the Formula (I) thus obtained is extracted with ethylacetate. Thereafter rosuvastatin is transformed into isopropylammonium or cyclohexylammonium salt in acetonitrile or ethylacetate. Said ammonium salts are converted into the sodium salt in an aqueous solution, which is transformed into rosuvastatin calcium salt using methods known in the state of the art.

Published International Patent Application WO2005077916 discloses rosuvastatin ammonium salts in general wherein the cation is different from ammonium, methylammonium, ethylammonium, diethanolammonium, (tris-hydroxymethyl)-methylammonium, benzylammonium or 4-methoxy-benzylammonium. Crystalline and amorphous rosuvastatin cyclohexyl-, dicyclohexyl-, isopropyl-, diisopropyl- and (S)-1-methylbenzylammonium salts are disclosed. The ammonium salts are prepared starting from rosuvastatin of the Formula (I) in ethylacetate solvent.

In Published International Patent Application WO 2006136407, a method for the preparation of rosuvastatin calcium salt of the Formula (IV) in amorphous form has been disclosed, which uses a rosuvastatin salt of the Formula (II) formed with an organic ammonium cation

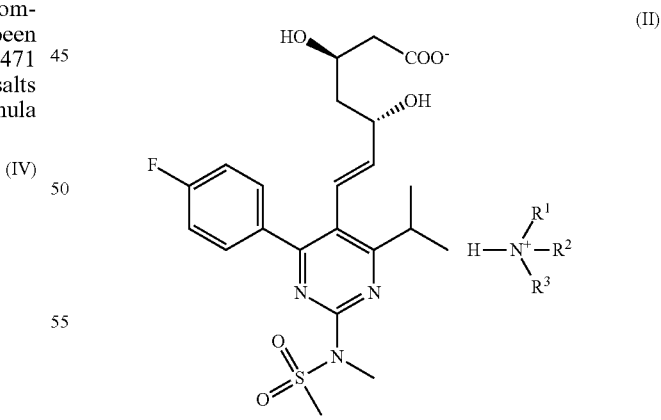

(II)

as starting material. The application discloses and claims several rosuvastatin ammonium salts, such as pyrrollidinium, piperidinium, morpholinium, adamantylammonium, N,N-dicyclohexylammonium, N-methyl-cyclohexylammonium, tert-octylammonium salts. The ammonium salts are prepared starting from a rosuvastatin ester or from rosuvastatin lactone of the Formula (VII)

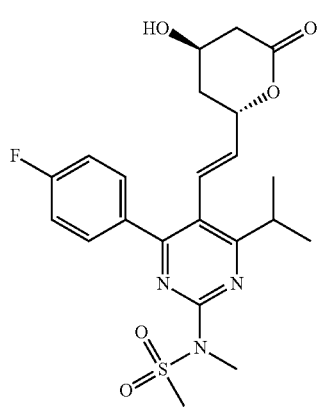

(VII)

by reacting said compound with the corresponding amine in aqueous solution or in the mixture of water and tetrahydrofurane. Preparation of several organic ammonium salts including rosuvastatin tert-butylammonium (TBA) salt of the Formula (IIa)

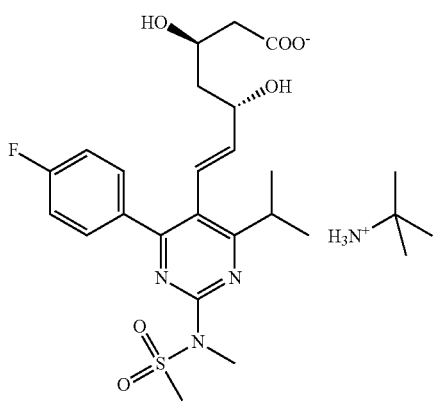

(IIa)

have been disclosed in the examples. However, no physical-chemical or analytical data for rosuvastatin TBA salt have been disclosed. According to the methods disclosed in the above-mentioned application, rosuvastatin TBA salt of the Formula (IIa) has not been used directly as a starting material for the preparation of rosuvastatin calcium salt of the Formula (IV).

Published International Patent Application WO 2007125547 discloses a "one-pot" method for the preparation of rosuvastatin of the Formula (I) or rosuvastatin ammonium salts of the Formula (II). Ammonium salts are prepared by subjecting rosuvastatin ketal tert-butylester of the Formula (VIII)

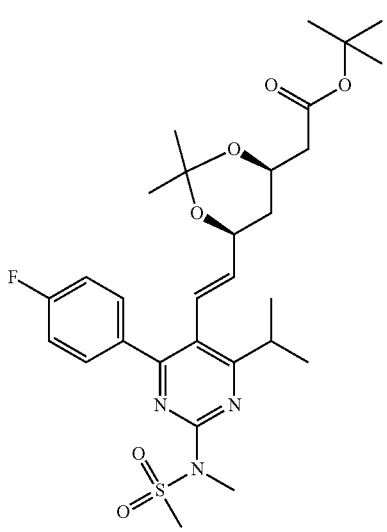

(VIII)

to acidic and subsequently alkaline hydrolysis, transforming the thus obtained rosuvastatin sodium salt of the Formula (VI)

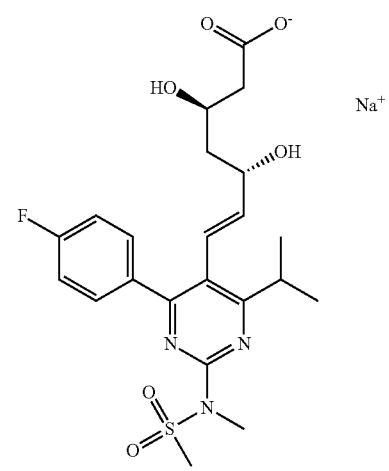

(VI)

into rosuvastatin of the Formula (I) and reacting rosuvastatin with the corresponding amine. Ammonium salt formation is carried out in acetonitrile.

Published International Patent Application WO2007000121 discloses a method for the preparation of rosuvastatin calcium salt of the Formula (IV) in amorphous or crystalline form starting—among others—from an amide of rosuvastatin formed with a primary amine. Rosuvastatin methylamide corresponding to the general Formula (III)

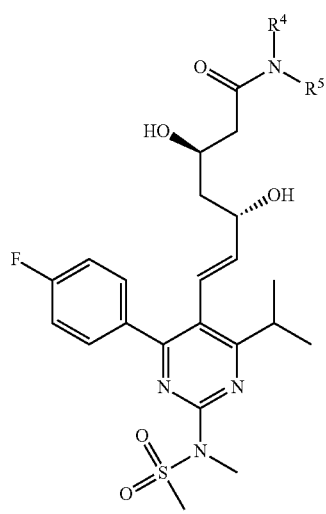

(III)

wherein R⁴ is methyl, R⁵ is hydrogen, is hydrolysed for 17 hours with an inorganic base—lithium hydroxide—in aqueous tetrahydrofurane solution at the temperature of 60° C.

In Published International Patent Application WO 2007125547, alkaline hydrolysis of rosuvastatin amides formed with secondary amines has been described using an alkali metal hydroxide, preferably sodium hydroxide. Among the amides of rosuvastatin, diisopropylamide is referred to specifically. The alkali metal salt obtained is transformed into rosuvastatin of the Formula (I) by acidification and subsequently converted into the corresponding ammonium salt using organic bases. Finally the ammonium salt is transformed into the sodium salt of the Formula (VI), which is finally converted into the calcium salt of the Formula (IV). The application furthermore discloses a crystalline form of rosuvastatin TBA salt of the Formula (IIa), which is characterized by an X-ray diffractogram. However, the disclosed purification method is complicated to carry out, several organic solvents are required for the extraction and during the crystallization of the TBA salt, it is necessary that the organic solvent be introduced in portions and it is required that after each addition except the final one, the solvent be removed by evaporation.

Published International Patent Application WO 2008044243 is related to a one-pot method for the preparation of rosuvastatin calcium salt of the Formula (IV), which comprises alkaline hydrolysis of rosuvastatin n-butylamide or rosuvastatin diizopropylamide by boiling with aqueous sodium hydroxide in ethyleneglycol. The alkali metal salt thus obtained is treated with an acid in water-ethylacetate solvent system and rosuvastatin of the Formula (I) thus obtained is converted into an organic ammonium salt by reacting with the corresponding organic base. Ammonium salt of rosuvastatin is thereafter converted into the sodium salt, which is transformed into rosuvastatin calcium salt of the Formula (IV).

Published International Patent Application WO 2005123082 is related to a combined pharmaceutical preparation consisting of rosuvastatin and acipimox. Among many other salt forms of rosuvastatin, rosuvastatin zinc salt is mentioned. However neither physical-chemical parameters of rosuvastatin zinc salt, nor a method of preparation thereof, or the stoichiometry of the salt have been disclosed.

Rosuvastatin zinc (2:1) salt of the Formula (V)

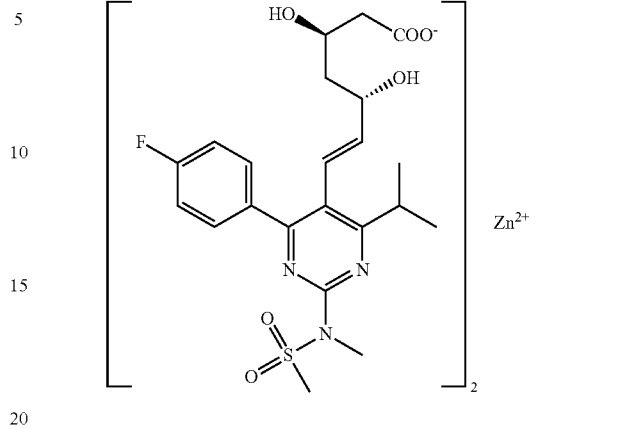

(V)

as well as methods for preparation thereof and physical-chemical properties of the same have been disclosed for the first time in Published International Patent Application WO 2007119085.

Published International Patent Application WO 2008015563 is related to the preparation of rosuvastatin zinc (2:1) salt of the Formula (V) starting from rosuvastatin tert-butylester of the Formula (IX)

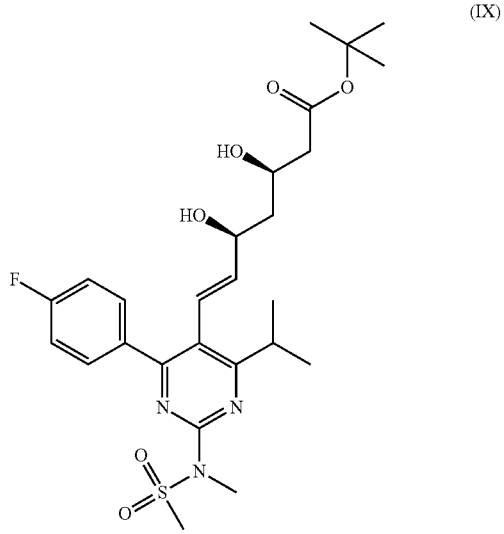 [SMILES: CC(C)c1nc(N(C)S(C)(=O)=O)nc(-c2ccc(F)cc2)c1/C=C/[C@@H](O)C[C@@H](O)CC(=O)OC(C)(C)C]

(IX)

as well as from rosuvastatin tert-butylammonium salt by transforming either starting material first into rosuvastatin sodium salt of the Formula (VI).

Published International Patent Application WO 2009047577 is related to a method for the preparation of rosuvastatin zinc salt of the Formula (V), wherein rosuvastatin of the Formula (I), sodium salt or an alkylester thereof, rosuvastatin lactone of the Formula (VII) or rosuvastatin ketal tert-butylester have been used as starting materials.

In published International Patent Application WO 2010082072, methods are disclosed for converting rosuvastatin TBA salt of the Formula (IIa) into rosuvastatin calcium salt of the Formula (IV) or rosuvastatin zinc salt of the Formula (V) using ethylacetate-water solvent system.

It is well known according to the state of the art that compounds belonging to the group of statins are easily transformed into their lactone form already at room temperature. Among others, published International Patent Application WO 2005077916 discloses the transformation of rosuvastatin diisopropylammonium salt into rosuvastatin lactone at pH 3 at the boiling temperature of toluene in six hours. Under such conditions, rosuvastatin ammonium salts (and analogously the calcium salt) undergo transformation into rosuvastatin of the Formula (I) in the first step, which is subsequently converted into rosuvastatin lactone of the Formula (VII) with full conversion. The observation that the lactonization takes place even at room temperature in an organic solvent with significant reaction rate is supported by experimental data. It has been found that the concentration of the lactone impurity rapidly exceeds the limit value prescribed by ICH Guidelines. Furthermore, it has been established by experimental evidence that the rate of lactonization is several times higher in acidic aqueous medium than in an organic solvent.

In most of the methods discussed above, rosuvastatin ammonium salts of the general Formula (II) are produced from rosuvastatin of the Formula (I) obtained in acidic media. The common disadvantages of these methods resides in that besides the extra step in the technology, the rate of lactonization in an acidic media is high which results in the decrease of yield and the contamination of the product.

During the transformation of rosuvastatin ammonium salts into rosuvastatin calcium salt of the Formula (IV) or rosuvastatin zinc salt of the Formula (V) according to the methods discussed above, the concentration of the lactone impurity usually remains unchanged, therefore the lactone impurity present in an intermediate of the general Formula (II) will appear in the drug substance as well as in the finished drug product.

In the methods according to the state of the art starting from a rosuvastatin amide of the general Formula (III), the hydrolysis of the amide is carried out in the presence of an alkali metal- or an alkali earth metal hydroxide and the reaction is carried out in an organic solvent. In this way, during the first step, a rosuvastatin salt with the specific alkali metal or alkali earth metal is formed, which requires further purification. However, since there are no suitable methods known in the state of the art for the purification of an alkali metal or alkali earth metal salt of rosuvastatin, the purification can be advantageously carried out by transforming the alkali metal or alkali earth metal salt of rosuvastatin into an ammonium salt of the same and purifying the ammonium salt by crystallization. Reacting the purified ammonium salt with an alkali metal hydroxide subsequently yields an alkali metal salt of rosuvastatin, preferably rosuvastatin sodium salt of the Formula (VI), which is transformed in the last step into rosuvastatin calcium salt by reacting with an inorganic calcium compound.

In conclusion, methods known according to the state of the art starting from a rosuvastatin amide of the general Formula (III) include extra steps in the technology, thus decreasing the efficiency and economy of the manufacturing process, the reagents and solvents are environmentally harmful and potential byproducts increase the contamination of the product. It can also be concluded that the purity of the final product is greatly influenced by the purity of the rosuvastatin ammonium salt of the general Formula (II) used in the manufacturing process.

The state of the art is silent about a method which is suitable for directly transforming a rosuvastatin amide of the general Formula (III) into a rosuvastatin ammonium salt of the general Formula (II), rosuvastatin calcium salt of the Formula (IV) or rosuvastatin zinc salt of the Formula (V), respectively.

SUMMARY OF THE INVENTION

The objective of our research-development work was to provide a method which is suitable for the direct transformation of rosuvastatin amides of the general Formula (III) formed with a primary or secondary amines into a rosuvastatin ammonium salt of the general Formula (II).

More specifically, our aim was to provide a method for producing rosuvastatin ammonium salts of the general Formula (II), which is suitable for the manufacture of rosuvastatin calcium salt of the Formula (IV) or rosuvastatin zinc salt of the Formula (V) therefrom. We have found that such especially preferable salts include crystalline and amorphous forms of rosuvastatin tert-butylammonium (TBA) salt of the Formula (IIa) and rosuvastatin n-butylammonium (NBA) salt of the Formula (IIb).

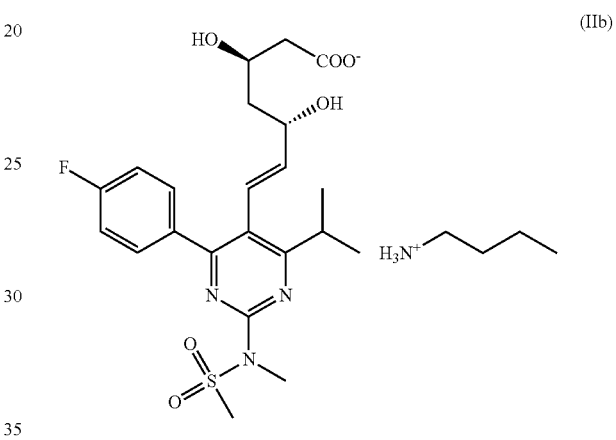

A further objective was to prevent formation of impurities, especially lactone formation by selecting appropriate reaction conditions during the process.

The above objective has been solved according to the present invention.

It is well known from the state of the art that amides, similarly to esters, can be hydrolysed using acidic or basic catalysts. In case of amides, however, the reaction requires more severe reaction conditions than in case of esters. No hydrolysis of amides takes place in the presence of water solely. Hydrolysis of an amide requires the presence of strong (inorganic) base or acid and prolonged heating (March's Advanced Organic Chemistry, 5$^{th}$ edition, Michael B. Smith and Jerry March, Ed.; Wiley, 2007, 474-476. old.).

We have very surprisingly found that the hydrolysis of a rosuvastatin amide of the general Formula (III) wherein $R^4$ and $R^5$ independently represent hydrogen or a saturated straight, branched or cyclic alkyl group comprising 1 to 6 carbon atoms, or $R^4$, $R^5$ together with the nitrogen attached thereto forms a saturated 5-, 6- or 7-membered saturated heterocyclic group containing one nitrogen, can be carried out in the absence of strong inorganic bases, e.g. alkali metal or alkali earth metal hydroxides. We observed that such starting materials react with organic amines and in the reaction the corresponding rosuvastatin ammonium salts of the general Formula (II) are obtained in aqueous or aqueous-organic solutions. The work-up of the reaction mixture can be carried out simply by evaporating in vacuo, thus the rosuvastatin ammonium salt of the general Formula (II) can be obtained in good yield and in high purity.

BRIEF DESCRIPTION OF THE DRAWING

FIG. 1: Powder X-ray diffractogram of Form II rosuvastatin tert-butylammonium salt of the Formula (IIa).

DETAILED DESCRIPTION OF THE INVENTION

According to the first aspect of the present invention, there is provided a method for the preparation of rosuvastatin calcium salt of the Formula (IV), which comprises reacting a rosuvastatin amide of the general Formula (III)

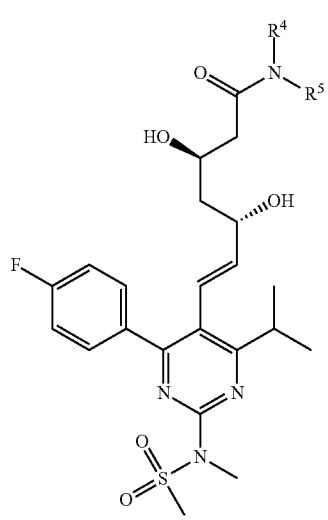

(III)

wherein $R^4$ and $R^5$ independently represents hydrogen or a saturated straight, branched or cyclic alkyl group comprising 1 to 6 carbon atoms, or $R^4$, $R^5$ together with the nitrogen attached thereto forms a 5-, 6- or 7-membered saturated heterocyclic group containing one nitrogen, in water or in a homogeneous mixture of water and a water-miscible organic solvent with a compound of the general Formula (X)

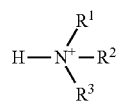

(X)

wherein $R^1$, $R^2$ and $R^3$ independently represents hydrogen or a saturated straight, branched or cyclic alkyl group comprising 1 to 6 carbon atoms, or $R^1$ and $R^2$ together with the nitrogen attached thereto forms a saturated 5-, 6- or 7-membered saturated heterocyclic group containing one nitrogen and $R^3$ represents hydrogen, and converting the thus obtained rosuvastatin ammonium salt of the general Formula (II) wherein $R^1$, $R^2$ and $R^3$ independently represents hydrogen or a saturated straight or branched alkyl group or a cycloalkyl group comprising 1 to 6 carbon atoms, or $R^1$ and $R^2$ together with the nitrogen attached thereto forms a saturated 5-, 6- or 7-membered heterocyclic group containing one nitrogen and $R^3$ represent hydrogen in a known manner into rosuvastatin calcium salt.

According to a preferable embodiment of the method, rosuvastatin calcium salt of the Formula (IV) is prepared by reacting a rosuvastatin amide of the general Formula (III) wherein the meaning of $R^4$ and $R^5$ is as defined above, in water or in a homogeneous mixture of water and a water miscible organic solvent with tert-butylamine and the thus directly obtained rosuvastatin tert-butylammonium (TBA) salt of the Formula (IIa) is transformed in known manner into rosuvastatin calcium salt.

According to a further preferable embodiment of the method, there is provided a method for preparing rosuvastatin calcium salt of the Formula (IV), which comprises reacting a rosuvastatin amide of the general Formula (III)—wherein the meaning of $R^4$ and $R^5$ is as defined above—in water or in a homogeneous mixture of water and a water-miscible organic solvent with n-butylamine and transforming the thus directly obtained rosuvastatin n-butylammonium salt of the Formula (IIb) into rosuvastatin calcium salt of the Formula (IV) according to methods known in the art.

According to the second aspect of the present invention, there is provided a method for the preparation of rosuvastatin zinc salt of the Formula (V) which comprises reacting a rosuvastatin amide of the general Formula (III)

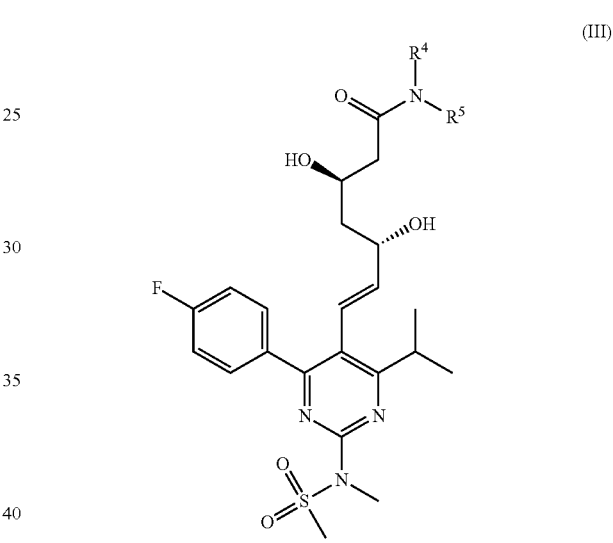

(III)

wherein $R^4$ and $R^5$ independently represents hydrogen or a saturated straight, branched or cyclic alkyl group comprising 1 to 6 carbon atoms, or $R^4$, $R^5$ together with the nitrogen attached thereto forms a 5-, 6- or 7-membered saturated heterocyclic group containing one nitrogen, in water or in a homogeneous mixture of water and a water-miscible organic solvent with a compound of the general Formula (X)

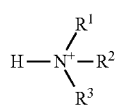

(X)

wherein $R^1$, $R^2$ and $R^3$ independently represents hydrogen or a saturated straight, branched or cyclic alkyl group comprising 1 to 6 carbon atoms, or $R^1$ and $R^2$ together with the nitrogen attached thereto forms a saturated 5-, 6- or 7-membered saturated heterocyclic group containing one nitrogen and $R^3$ represents hydrogen, and converting the thus obtained rosuvastatin ammonium salt of the general Formula (II) wherein $R^1$, $R^2$ and $R^3$ independently represents hydrogen or a saturated straight or branched alkyl group or a cycloalkyl group comprising 1 to 6 carbon atoms, or $R^1$ and $R^2$ together with the nitrogen attached thereto forms a saturated 5-, 6- or 7-membered heterocyclic group containing one nitrogen and $R^3$ represent hydrogen in a known manner into rosuvastatin zinc salt.

According to a preferable embodiment of the method, a rosuvastatin amide of the general Formula (III)—wherein the meaning of $R^4$ and $R^5$ are as defined above—is reacted in water or in a homogeneous mixture of water and a water-miscible organic solvent with n-butylamine and transforming rosuvastatin n-butylammonium salt of the Formula (IIb) thus directly obtained into rosuvastatin zinc salt of the Formula (V) according to methods known from the art.

A further preferable embodiment of the method for the preparation of rosuvastatin zinc salt the Formula (V) comprises reacting a rosuvastatin amide of the general Formula (III)—wherein the meaning of $R^4$ and $R^5$ is as defined above—with tert-butylamine in water or in a homogeneous mixture of water and a water-miscible organic solvent and transforming the thus directly obtained rosuvastatin tert-butylammonium salt of the Formula (IIa) into rosuvastatin zinc salt of the Formula (V) according to methods known in the art.

A further subject of the present invention is a method for the preparation of compounds of rosuvastatin formed with amines corresponding to general Formula (II), wherein $R^1$, $R^2$ and $R^3$ independently represents hydrogen or a saturated straight, branched or cyclic alkyl group comprising 1 to 6 carbon atoms, or $R^1$ and $R^2$ together with the nitrogen attached thereto forms a 5-, 6- or 7-membered saturated heterocyclic group containing one nitrogen and $R^3$ represents hydrogen, which comprises reacting a rosuvastatin amide of the general Formula (III) wherein $R^4$ and $R^5$ independently represents hydrogen or a saturated straight, branched or cyclic alkyl group comprising 1 to 6 carbon atoms or $R^4$, $R^5$ together with the nitrogen attached thereto forms a 5-, 6- or 7-membered saturated heterocyclic group containing one nitrogen with a compound of the general Formula (X) wherein $R^1$, $R^2$ and $R^3$ independently represents hydrogen or a saturated straight, branched or cyclic alkyl group comprising 1 to 6 carbon atoms, or $R^1$ and $R^2$ together with the nitrogen attached thereto forms a 5-, 6- or 7-membered saturated heterocyclic group containing one nitrogen and $R^3$ represents hydrogen in water or in a homogeneous mixture of water and a water-immiscible organic solvent and isolating the thus obtained compound of the general Formula (II).

According to a still further aspect of the present invention, there is provided a one-step method for the preparation of rosuvastatin tert-butylammonium (TBA) salt of the Formula (IIa) starting from a rosuvastatin amide of the general Formula (III)—wherein the meaning of $R^4$ and $R^5$ is as defined above—by reacting a compound of the Formula (III) with tert-butylamine in water or in a homogeneous mixture of water and a water-miscible organic solvent.

According to a still further aspect of the present invention, there is provided a one-step method for the preparation of rosuvastatin n-butylammonium (NBA) salt of the Formula (IIb) starting from a rosuvastatin amide of the general Formula (III)—wherein the meaning of $R^4$ and $R^5$ is as defined above—by reacting a compound of the Formula (III) with n-butylamine in water or in a homogeneous mixture of water and a water-miscible organic solvent.

In the present specification, under the expression "rosuvastatin salt of the Formula (II)" or "rosuvastatin ammonium salt of the Formula (II)", compounds comprising rosuvastatin anion and an ammonium cation in 1:1 molar ratio, amorphous and crystalline forms, hydrates and solvates thereof are meant wherein $R^1$, $R^2$ and $R^3$ independently represents hydrogen or a straight, branched or cyclic alkyl group comprising 1 to 6 carbon atoms or $R^1$ and $R^2$ together with the nitrogen attached thereto comprises a 5-, 6- or 7-membered saturated heterocyclic group comprising one nitrogen atom and $R^3$ is hydrogen.

In the present specification, the expression "rosuvastatin amide of the general Formula (III)" or "rosuvastatin amide of the Formula (III)" refers to compounds of the general Formula (III), including amorphous or crystalline forms, hydrates or solvates thereof, wherein $R^4$ and $R^5$ independently from each other represents hydrogen or a straight, branched or cyclic alkyl group comprising 1 to 6 carbon atoms or $R^4$, $R^5$ together with a nitrogen atom attached thereto forms a 5-, 6- or 7-membered saturated heterocyclic group containing one nitrogen atom.

Under the expression "rosuvastatin n-butylamide" the compound (3R,5S,6E)-N-butyl-7-{4-(4-fluorophenyl)-6-(1-methylethyl)-2-[methyl(methylsulfonyl)amino]pyrimidin-5-yl}-3,5-dihydroxyhept-6-eneamide of the Formula (IIIa) is meant. Under the expression "rosuvastatin N,N-dimethylamide", the compound (3R,5S,6E)-7-{4-(4-fluorophenyl)-6-(1-methylethyl)-2-[methyl(methylsulfonyl)-amino]pyrimidin-5-yl}-3,5-dihydroxy-N,N-dimethylhept-6-eneamide of the Formula (IIIb) is meant. Under the expression "rosuvastatin pyrrolidinylamide", N-{5-[(1E,3S,5R)-3,5-dihydroxy-7-oxo-7-pyrrolidin-1-yl-hept-1-en-1-yl]-4-(4-fluorophenyl)-6-(1-methylethyl)-pyrimidin-2-yl}-N-methylmethanesulfonamide of the Formula (IIIc) is meant.

In the present specification, the meaning of the expression "rosuvastatin calcium salt of the Formula (IV)" is the compound consisting of rosuvastatin anion and calcium(II) cation in 2:1 molar ratio including amorphous and crystalline forms, hydrates and solvates thereof.

In the present specification, the meaning of the expression "rosuvastatin zinc salt of the Formula (V)" is the compound comprising rosuvastatin anion and zinc (II) cation in 2:1 molar ratio including amorphous and crystalline forms, hydrates and solvates thereof.

In the present specification, the expression "homogeneous mixture of water and a water-miscible solvent" means a solvent mixture having one phase (one solvent layer) in the state when no dissolved compounds are present, and the solvent mixture is comprised of water and a water-miscible solvent.

In the present specification, the expression "aliphatic alcohols having 1 to 6 carbon atoms" means monohydric saturated aliphatic alcohols having one to six carbon atoms, e.g. methanol, ethanol, 1-propanol, 2-propanol and the like.

In the method according to the present invention, a rosuvastatin amide of the general Formula (III)—wherein the meaning of $R^4$ and $R^5$ is as defined above—is transformed directly in one reaction step into a rosuvastatin ammonium salt of the general Formula (II), preferably into rosuvastatin TBA salt of the Formula (IIa) or rosuvastatin NBA salt of the Formula (IIb).

The method according to the present invention is carried out by reacting a rosuvastatin amide of the general Formula (III)—wherein the meaning of $R^4$ and $R^5$ is as defined above—in water or in a homogeneous mixture of water and a water miscible solvent, preferably in a mixture with a water-soluble alcohol comprising 1 to 6 carbon atoms, the most preferably in water at a temperature between 80 and 140° C., preferably between 110 and 130° C. with 1 to 30 molar equivalents, preferably 20 molar equivalents of primary or secondary amine of the Formula (X)—wherein the meaning of $R^1$, $R^2$ and $R^3$ is as defined above—, preferably with tert-butylamine or n-butylamine for 16 to 30 hours. After the reaction, water is removed by evaporation and the residue is crystallized. The crude rosuvastatin salt of the Formula (II) thus obtained—wherein the meaning of $R^1$, $R^2$ és $R^3$ is as defined above—can optionally be purified by triturating, crystallizing or the combination thereof.

The advantage of the method according to the present invention resides in the fact that the hydrolysis is performed in an aqueous medium, optionally in the absence of an organic solvent, therefore the environmental exposure is low and no cost for organic solvents is incurred. During the work-up of the reaction mixture, rosuvastatin TBA salt of the Formula (IIa) and rosuvastatin NBA salt of the Formula (IIb) are isolated directly without any further steps. It is surprising that rosuvastatin TBA and NBA salts, respectively, are obtained in high yield (approx. 90%). It has unexpectedly observed that despite of the high reaction temperature, rosuvastatin TBA and NBA salts, respectively, are obtained in good purity (in excess of 92%) even as crude products. After purification (trituration, recrystallization), the purity of the product is higher than 99.5%, which satisfies the ICH requirements. Rosuvastatin TBA salt of the Formula (IIa) and rosuvastatin NBA salt of the Formula (IIb) can be used as intermediates in the manufacture of rosuvastatin calcium salt of the Formula (IV) and rosuvastatin zinc salt of the Formula (V).

We have found that according to the circumstances of the work-up of the reaction mixture and product isolation, rosuvastatin TBA salt of the Formula (IIa) can be produced either as Form I rosuvastatin TBA already known in the state of the art or as Form II rosuvastatin TBA salt. Crystalline Form II Rosuvastatin TBA salt as produced and characterized according to the method of Example 1, Method "D" is new. Crystalline Form II rosuvastatin salt has advantageous solubility in different solvents and can be produced in high purity. It can also be used in the preparation of rosuvastatin salts of the Formulae (IV) and (V), respectively.

Crystalline Form II rosuvastatin TBA salt has been characterized by powder X-ray diffraction analysis. The results are shown in Example 1 under the heading "Method D". In the powder X-ray diffractogram of crystalline Form II rosuvastatin TBA salt measured with copper $K_\alpha$ X-ray source, the most intense reflexion occurred at 18.654 degrees 2Θ (±0.2 degrees 2Θ). Reflexions exceeding 60% of the intensity of the basic reflexion at 18.654 degrees occur at 15.803 and 18.654 degrees 2Θ (±0.2 degrees 2Θ). Reflexions having higher relative intensity than 30% of the basic reflexion can be measured at 11.282, 15.803 and 18.654 degrees 2Θ (±0.2 degrees 2Θ).

Thus, according to the method of the present invention, amides of rosuvastatin formed with primary or secondary amines are directly transformed into high-purity rosuvastatin ammonium salts of the general Formula (II) using aqueous solvent, in the absence of environmentally harmful solvents in a simple way easily adoptable for industrial manufacture.

Further details of the present invention are demonstrated by the following examples without limiting the invention to the examples in any way.

Example 1

Preparation of rosuvastatin tert-butylammonium salt starting from rosuvastatin n-butylamide Method "A":

A 800 cm$^3$ autoclave is charged with 16.1 g (0.03 mol) of rosuvastatin n-butylamide, 644 cm$^3$ of water and 43.9 g (63.3 cm$^3$; 0.60 mol) tert-butylamine. The reaction mixture is stirred for 24 hours at 120° C. The mixture is allowed to cool to room temperature, diluted with 2-propanol and evaporated in vacuo. The residue is stirred in the mixture of tert-butylmethylether and heptane (2:5, v/v) and the crystals are filtered. Thus 16.2 g (99%) of rosuvastatin TBA salt are obtained. The crude salt is boiled in acetonitrile/2-propanol (8.6:1, v/v) mixture, subsequently further stirred at room temperature, filtered, washed and dried. The product thus obtained is boiled in acetonitrile, 2-propanol is added to the boiling mixture, decolorized with carbon and filtered. The precipitated crystals are filtered and washed with acetonitrile. Yield 10.9 g (66%) rosuvastatin TBA salt having the purity (as determined by high-performance liquid chromatography, HPLC) exceeds 99.5%.

Method "B":

An autoclave having 800 cm$^3$ volume is charged with 16.1 g (0.03 mol) of rosuvastatin n-butylamide, 644 cm$^3$ of water/ethanol (9:1, v/v) solvent mixture and 43.9 g (63.3 cm$^3$; 0.60 mol) tert-butylamine. The reaction mixture is stirred for 24 hours at 120° C. The mixture is allowed to cool to room temperature, diluted with 2-propanol and evaporated in vacuo. The evaporation residue is stirred in the mixture of tert-butylmethylether and heptane (2:5, v/v) and the crystals are filtered. Thus 16.7 g (100%) of rosuvastatin TBA salt are obtained. The crude salt is boiled in the mixture of acetonitrile and 2-propanol (8.6:1, v/v), stirred at room temperature, filtered, washed and dried. The product thus obtained is boiled in acetonitrile, 2-propanol are added to the boiling mixture, decolorized with carbon and filtered. The precipitated crystals are filtered and washed with acetonitrile. In this way 10.7 g (64%) of rosuvastatin TBA salt having a purity (as determined by HPLC) greater than 99.5% are obtained.

Method "C":

An autoclave having 800 cm$^3$ volume is charged with 16.1 g (0.03 mol) rosuvastatin n-butylamide, 644 cm$^3$ of water and 43.9 g (63.3 cm$^3$; 0.60 mol) of tert-butylamine. The reaction mixture is stirred for 28 hours at the temperature of 110° C. The mixture is allowed to cool to room temperature, diluted with 2-propanol and evaporated in vacuo. The evaporation residue is boiled in acetonitrile/2-propanol (8.6:1, v/v), further stirred at room temperature, filtered, washed and dried. The product thus obtained is boiled in acetonitrile, 2-propanol are added, decolorized with carbon and filtered. The precipitated crystals are filtered and washed with acetonitrile. Thus 10.3 g (65%) of rosuvastatin TBA salt having the purity (as determined by HPLC) exceeding 99.5%.

Method "D":

An autoclave having 800 cm$^3$ volume is charged with 16.1 g (0.03 mol) rosuvastatin n-butylamide, 644 cm$^3$ of water and 43.9 g (63.3 cm$^3$; 0.60 mol) tert-butylamine. The reaction mixture is stirred for 24 hours at the temperature of 120° C. The reaction mixture is allowed to cool to room temperature, diluted with 2-propanol and evaporated in vacuo. The residue is stirred in tert-butylmethylether-heptane mixture (2:5, v/v) and the crystals are filtered. Thus 16.2 g (99%) of crude rosuvastatin TBA salt are obtained. The crude salt is boiled in the mixture of acetonitrile and 2-propanol (8.6:1, v/v), stirred at room temperature, filtered, washed and dried. The product thus obtained is suspended in water and tert-butylamine (13 cm$^3$) are added. The mixture is allowed to stand for four days and filtered. The mother lye is allowed to stand for further three days and the precipitated product is filtered, washed and dried. In this way, 4.33 g (25%) Form II rosuvastatin tert-butylammonium salt having the powder X-ray diffractogram of FIG. 1 are obtained.

Apparatus and measurement conditions for X-ray diffractometry

Apparatus: BRUKER D8 ADVANCE powder diffractometer
Radiation: CuKα$_1$ (λ=1.54060 Å), CuKα$_2$ (λ=1.54439 Å)
Voltage: 40 kV Anode current: 30 mA
Accessories: Göbel-mirror
 Soller-slit
 Sampler, transmission position
Detector: LynxEye
Measurement: continous Θ/Θ scan: 4-35 2Θ°
Step size: 0.02°
Sample: untreated (no pulverization), measured at room temperature X-ray diffraction signals of Form II rosuvastatin TBA salt of the Formula (IIa) are summarized in Table 1.

TABLE 1

| Peak No. | Angle 2-Theta (degrees) | d value Angstroms | Intensity % |
| --- | --- | --- | --- |
| 1 | 5.481 | 16.11132 | 8.1 |
| 2 | 5.957 | 14.82335 | 7.1 |
| 3 | 10.529 | 8.39561 | 27.0 |
| 4 | 11.282 | 7.83634 | 31.4 |
| 5 | 15.457 | 5.72793 | 16.8 |
| 6 | 15.803 | 5.60353 | 69.9 |
| 7 | 16.231 | 5.45656 | 13.7 |
| 8 | 16.682 | 5.31014 | 10.9 |
| 9 | 18.651 | 4.75363 | 100 |
| 10 | 19.05 | 4.65489 | 28.5 |
| 11 | 19.832 | 4.47316 | 31.4 |
| 12 | 20.512 | 4.32646 | 28.1 |
| 13 | 21.098 | 4.20759 | 12.5 |
| 14 | 22.492 | 3.94978 | 24.1 |
| 15 | 27.205 | 3.27526 | 14.6 |
| 16 | 30.409 | 2.93708 | 9.7 |

Example 2

Preparation of rosuvastatin tert-butylammonium salt starting from rosuvastatin N,N-dimethylamide Method "A": An autoclave having 50 cm³ volume is charged with 0.89 g (1.75 mmol) of rosuvastatin N,N-dimethylamide, 35.6 cm³ of water and 2.56 g (3.7 cm³; 3.5 mmol) tert-butylamine. The reaction mixture is stirred at 120° C. for 16 hours. The mixture is allowed to cool to room temperature, the reaction residue is diluted with ethanol in portions and evaporated in vacuo. The evaporation residue is stirred in a mixture of tert-butylmethylether and heptane (2:5 v/v, 4 cm³) and the crystals are filtered. Thus 0.87 g (90%) of rosuvastatin TBA salt are obtained. The crude salt is recrystallized from acetonitrile/2-propanol. Yield, 0.58 g (60%) rosuvastatin TBA salt having purity (by HPLC) exceeding 99.5%.

Method "B": An autoclave having 50 cm³ volume is charged with 0.89 g (1.75 mmol) rosuvastatin N,N-dimethylamide, 35.6 cm³ water-ethanol 9:1 (v/v) solvent mixture and 2.56 g (3.7 cm³; 3.5 mmol) of tert-butylamine. The reaction mixture is stirred at 120° C. for 16 hours, allowed to cool and at room temperature, ethanol is added portionwise and the mixture is evaporated. The residue is stirred in diethylether-hexane mixture (1:1, v/v) and the crystals are filtered. The product thus obtained is recrystallized from acetonitrile/2-propanol mixture (2:1, v/v). Yield, 0.58 g (60%) rosuvastatin TBA salt having purity as assayed by HPLC in excess of 99.5%.

Example 3

Preparation of rosuvastatin tert-butylammonium salt starting from rosuvastatin pyrrollidinylamide An autoclave having 50 cm³ volume is charged with 0.88 g (1.65 mmol) rosuvastatin pyrrolidinylamide, 35.2 cm³ of water and 2.41 g (3.5 cm³; 3.3 mmol) tert-butylamine. The mixture is stirred at 120° C. for 16 hours, allowed to cool to room temperature, diluted with ethanol in portions and evaporated in vacuo. The residue is stirred in a mixture of diethylether-hexane (1:1, v/v) and the crystals are filtered. The product thus obtained is recrystallized from acetonitrile/2-propanol (2:1, v/v). Yield, 0.55 g (60%) rosuvastatin TBA having a purity as assessed by HPLC exceeding 99.5%.

Example 4

Preparation of rosuvastatin n-butylammonium salt starting from rosuvastatin n-butylamide An autoclave having 800 cm³ is charged with 16.1 g (0.03 mol) rosuvastatin n-butylamide, 644 cm³ of water and 43.9 g (63.3 cm³; 0.60 mol) of n-butylamine. The reaction mixture is stirred at 120° C. for 24 hours, allowed to cool, diluted with 2-propanol at room temperature and evaporated in vacuo. The residue is boiled in ethylacetate, and while stirring, allowed to cool to room temperature. The crystals are filtered. Thus 14.8 g (89%) of rosuvastatin NBA salt are obtained. The crude salt is stirred in ethylacetate at room temperature, filtered, washed and dried. Thus dried product is boiled in ethylacetate, thereafter stirred in the same solvent at room temperature, filtered, washed and dried. Yield 9.32 g (56%) of rosuvastatin NBA salt, having purity (as determined by HPLC) exceeding 99.5%.

Example 5

Preparation of rosuvastatin zinc salt starting from rosuvastatin n-butylamide (via rosuvastatin tert-butylammonium salt intermediate)

An apparatus protected from light is charged with 6.15 g (0.011 mol) of rosuvastatin TBA salt produced according to Example 1, Method A and 370 cm³ of water at 20-25° C. and the salt is dissolved. Thereafter an argon atmosphere is established and solution of 2.15 g (0.012 mol) zinc sulfate monohydrate in 17.8 cm³ of distilled water are added thereto dropwise at 20-25° C. The suspension is cooled to 5-10° C., filtered and washed with distilled water. The wet product is stirred in distilled water under an argon atmosphere at 5-10° C. for 41 hours. The product is filtered, washed with distilled water several times and dried in vacuo protected from light. Yield 4.60 g (81%).

Example 6

Preparation of rosuvastatin calcium salt starting from rosuvastatin n-butylamide (via rosuvastatin tert-butylammonium salt)

1.67 g (3.0 mmol) of rosuvastatin TBA salt prepared according to Method A, Example 1 are placed in an apparatus protected from light into a mixture of 10 ml of water and 15 ml of ethylacetate at room temperature while stirring intensely. After complete dissolution, five times in 15-minute periods, 1.5 ml (5×7 5 mmol) of saturate calcium chloride solution are added dropwise into the two-layer solution. After the addition, the reaction mixture is stirred for a further hour. The upper ethylacetate layer is separated and washed with 5 ml of 2.0 M calcium chloride solution and twice with water. The organic layer is dried by azeotropic distillation. The ethylacetetate layer is evaporated and the white residue is dissolved in water-free ethylacetate. The solution is stirred for five minutes at 42-45° C. and evaporated to dryness at 50 mbar pressure. Cyclohexane is added to the dry residue and the suspension is stirred thoroughly. The solids are filtered, washed with dry cyclohexane and dried invacuo at the temperature of 50° C. Yield, 1.30 g (87%).

Reference Example 1

Preparation of rosuvastatin pyrrollidinylamide from rosuvastatin ethylester

A 100-cm³ round bottom flask is charged with 5.20 g (10.0 mmol) rosuvastatin ethylester, 15 cm³ of ethanol, 3.55 g (4.1 cm³; 50.0 mmol) pyrrolidine and a few crystals of p-toluenesulfonic acid. The reaction mixture is stirred at room temperature for 8 hours and the precipitated crystals are filtered. Thus 4.73 g (89%) of the title product are obtained.

Mp.: 162-164° C.

Assay (by HPLC): approx. 99%

1. Reference Example 2

Preparation of rosuvastatin N,N-dimethylamide from rosuvastatin ethylester

A 100-cm³ volume round bottom flask is charged with 5.20 g (10.0 mmol) rosuvastatin ethylester, 15 cm³ of ethanol, 27.4 cm³ (24.7 g/100 cm³; 150 mmol) dimethylamine solution in ethanol and a few crystals of p-toluenesulfonic acid. The reaction mixture is stirred at room temperature for 8 hours and evaporated in vacuo. The residue is crystallized from diethylether, the crystals are filtered, washed and dried. Thus 4.58 g (93%) of title product are obtained.

Mp.: 76-78° C.

Assay by HPLC: approx. 97%

Reference Example 3

Preparation of rosuvastatin n-butylamide from rosuvastatin methylester

A 250-cm³ volume round bottom flask is charged with 9.91 g (20.0 mmol) of rosuvastatin methylester, 30 cm³ of ethanol, 7.31 g (9.9 cm³; 100 mmol) of n-butylamine and a few crystals of p-toluenesulfonic acid. The reaction mixture is stirred at room temperature for 8 hours and evaporated in vacuo. The residue is dissolved in ethylacetate, washed with saturated sodium carbonate solution, dried and evaporated. The residue is crystallized from diethylether-hexane, the crystals are filtered. Thus 10.10 g (94%) of title compound are obtained.

Melting point, 106-109° C.

Assay (HPLC): 99.5%

What we claim is:

1. A method for the preparation of a rosuvastatin product, which method is one of the following methods I to V:
   I) for the preparation of rosuvastatin ammonium salt of Formula (II),

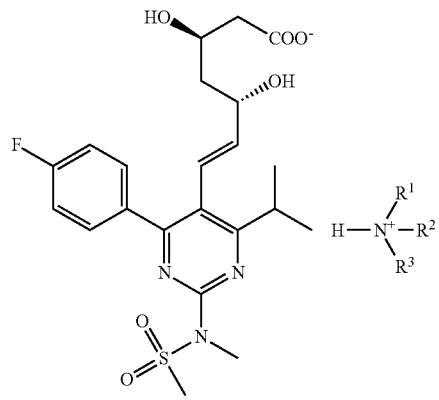

wherein $R^1$, $R^2$ and $R^3$ independently represent hydrogen or a straight, branched or cyclic saturated alkyl group comprising 1 to 6 carbons atoms or $NR^1R^2$ together represents a saturated heterocyclic group having 5, 6 or 7 carbon atoms and one nitrogen atom, which comprises reacting a rosuvastatin amide of Formula (III)

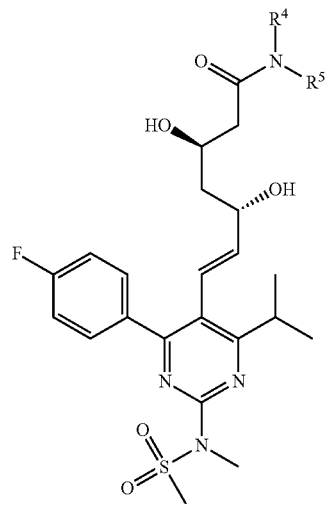

wherein $R^4$ and $R^5$ independently from each other represent hydrogen or a straight, branched or cyclic alkyl group comprising 1 to 6 carbon atoms or $NR^4R^5$ together represents a saturated 5, 6 or 7-membered heterocyclic group having one nitrogen atom, in water or in a homogeneous mixture of water and a water-miscible organic solvent, with an amine of the Formula (X)

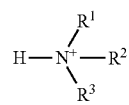

wherein $R^1$, $R^2$ and $R^3$ independently from each other represent hydrogen or a straight, branched or cyclic alkyl group comprising 1 to 6 carbon atoms, or $R^1$ and $R^2$ with the nitrogen attached thereto comprises a saturated 5, 6 or 7-membered heterocyclic group having one nitrogen atom;

or

II) for the preparation of rosuvastatin calcium salt of Formula (IV)

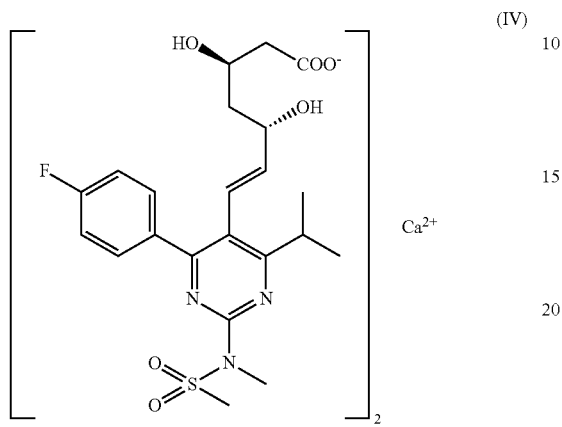

(IV)

which comprises
a) reacting a rosuvastatin amide of Formula (III),

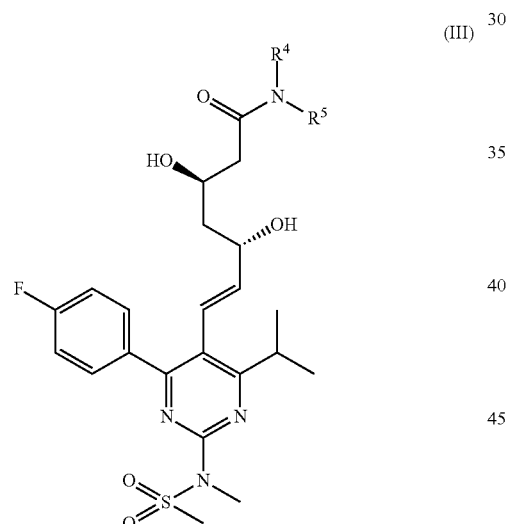

(III)

wherein $R^4$ and $R^5$ each independently represents hydrogen or a straight, branched or cyclic saturated alkyl group comprising 1 to 6 carbon atoms or $NR^4R^5$ together forms a saturated 5, 6 or 7-membered heterocyclic group having one nitrogen atom,
in water or in a homogeneous mixture of water and a water-miscible organic solvent,
with an amine of Formula (X)

(X)

wherein $R^1$, $R^2$ and $R^3$ independently represent hydrogen or a straight, branched or cyclic alkyl group comprising 1 to 6 carbon atoms or $R^1$ and $R^2$ together with a nitrogen atom attached thereto form a saturated 5, 6 or 7-membered heterocyclic group having one nitrogen;

b) transforming the rosuvastatin ammonium salt of Formula (II) obtained in step a),

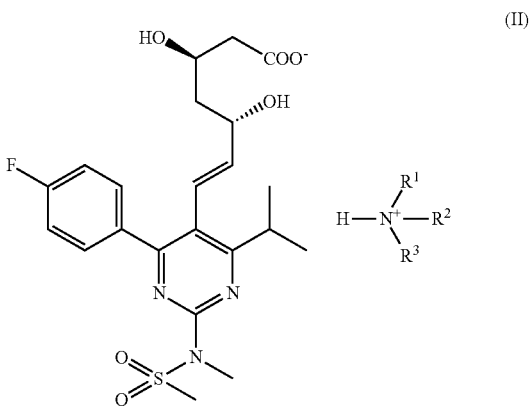

(II)

wherein $R^1$, $R^2$ and $R^3$ each independently from each other represents hydrogen or a straight, branched or cyclic saturated alkyl group comprising 1 to 6 carbon atoms or $R^1$ and $R^2$ together with the nitrogen attached thereto form a saturated 5, 6 or 7-membered heterocyclic group having one nitrogen atom, into rosuvastatin calcium salt of Formula (IV) or a hydrate form thereof;

or

III) for the preparation of rosuvastatin zinc (2:1) salt of Formula (V)

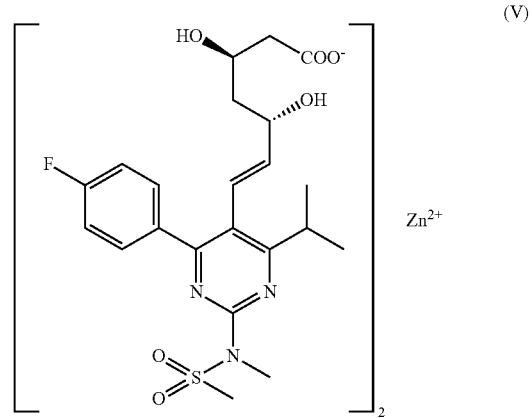

(V)

which comprises
a) reacting a rosuvastatin amide of Formula (III),

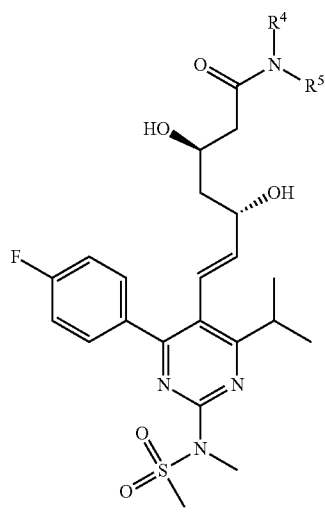

wherein R$^4$ and R$^5$ each independently from each other represents hydrogen or a straight, branched or cyclic alkyl group having 1 to 6 carbon atoms or NR$^4$R$^5$ together represents a saturated 5-, 6- or 7-membered heterocyclic group having one nitrogen,
in water or in a homogeneous mixture of water and a water-miscible organic solvent,
with an amine of Formula (X)

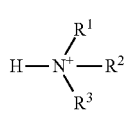

wherein R$^1$, R$^2$ and R$^3$ each independently from each other represents hydrogen or a straight, branched or cyclic alkyl group having one to six carbon atoms or R$^1$ and R$^2$ with a nitrogen atom attached thereto form a saturated 5, 6 or 7-membered heterocyclic group having one nitrogen atom;
b) transforming rosuvastatin ammonium salt of Formula (II) obtained in step a)

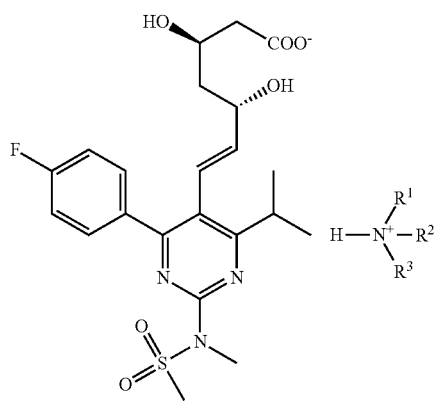

wherein R$^1$, R$^2$ and R$^3$ each independently from each other represents hydrogen or a straight, branched or cyclic alkyl group having 1 to 6 carbon atoms or R$^1$ and R$^2$ together with the nitrogen atom attached thereto form a saturated 5, 6 or 7-membered heterocycylic group having one nitrogen atom into rosuvastatin zinc (2:1) salt of Formula (V);
or
IV) for the preparation of rosuvastatin TBA salt of Formula (IIa) in crystalline Form II,

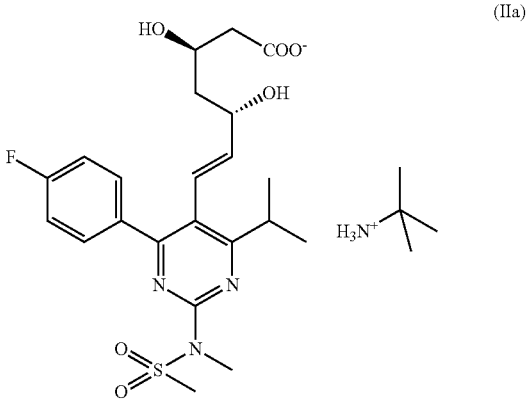

which comprises
a) reacting a rosuvastatin amide of Formula (III),

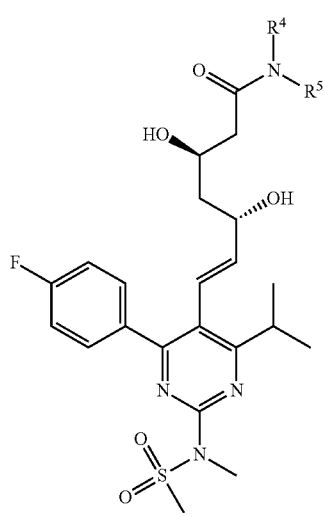

wherein R$^4$ and R$^5$ each independently from each other represents hydrogen or a straight, branched or cyclic alkyl group having 1 to 6 carbon atoms or wherein NR$^4$R$^5$ together represents a saturated 5-, 6- or 7-membered heterocyclic group having one nitrogen atom,
in water or in a homogeneous mixture of water and a water-miscible solvent,
with an amine of Formula (X)

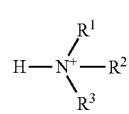

wherein R$^1$, R$^2$ and R$^3$ each independently from each other represents hydrogen or a straight, branched or cyclic alkyl group having 1 to 6 carbon atoms or R$^1$ and R$^2$ together with the nitrogen atom attached thereto form a saturated 5, 6 or 7-membered heterocycylic group having one nitrogen, b) purifying crude rosuvastatin TBA salt obtained in step a) by crystallization;

c) mixing the aqueous suspension of the purified rosuvastatin TBA salt of the Formula (IIa) thus obtained with tert-butylamine and d) crystallizing rosuvastatin TBA salt crystalline Form (II) of the Formula (IIa) fractionally;

or

V) for the preparation of rosuvastatin TBA salt of Formula (IIa),

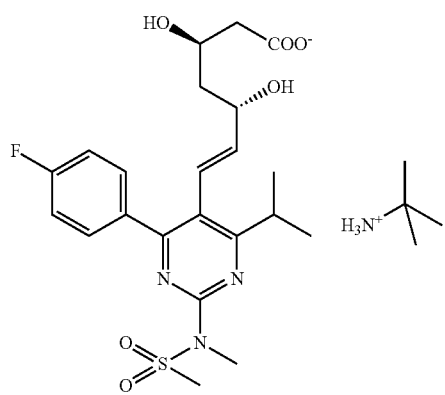

(IIa)

which comprises
reacting a rosuvastatin amide of Formula (III),

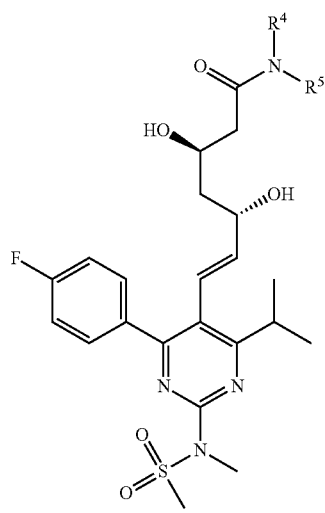

(III)

wherein $R^4$ and $R^5$ each independently from each other represents hydrogen or a straight, branched or cyclic alkyl group having 1 to 6 carbon atoms or wherein $NR^4R^5$ together represents a saturated 5-, 6- or 7-membered heterocyclic group having one nitrogen atom, in water or in a homogeneous mixture of water and a water-miscible solvent, with an amine of Formula (X)

(X)

wherein $R^1$, $R^2$ and $R^3$ each independently from each other represents hydrogen or a straight, branched or cyclic alkyl group having 1 to 6 carbon atoms or wherein $R^1$ and $R^2$ together with the nitrogen atom attached thereto form a saturated 5, 6 or 7-membered heterocyclic group having one nitrogen.

2. The method according to claim 1, which is the method I.

3. The method according to claim 2, wherein the rosuvastatin amide of Formula (III) is rosuvastatin n-butylamide of Formula (IIIa)

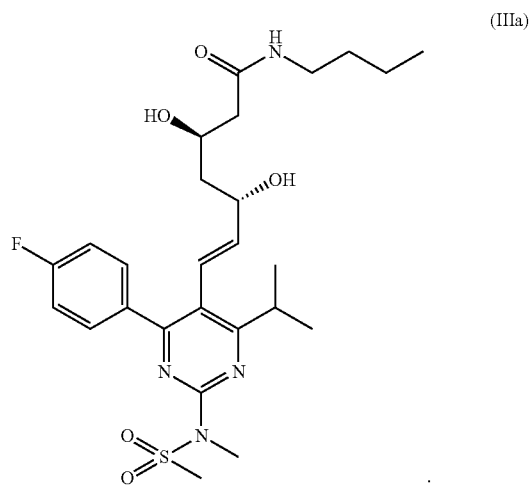 [SMILES: CCCCNC(=O)C[C@H](O)C[C@H](O)/C=C/c1c(-c2ccc(F)cc2)nc(N(C)S(C)(=O)=O)nc1C(C)C]

(IIIa)

4. The method according to claim 2, wherein the rosuvastatin amide of Formula (III) is rosuvastatin N,N-dimethylamide of Formula (IIIb)

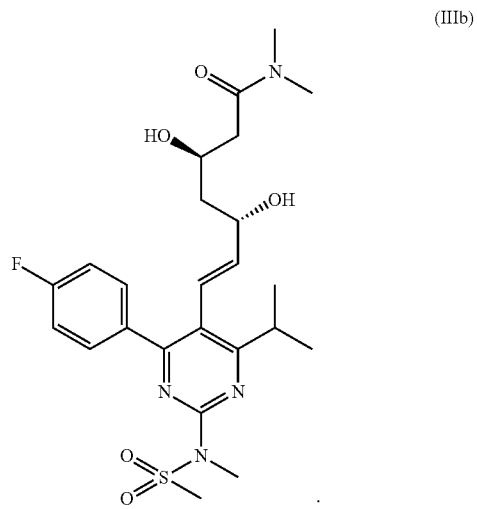 [SMILES: CC(C)c1nc(N(C)S(C)(=O)=O)nc(-c2ccc(F)cc2)c1/C=C/[C@@H](O)C[C@@H](O)CC(=O)N(C)C]

(IIIb)

5. The method according to claim 2, wherein the rosuvastatin amide of Formula (III) is rosuvastatin pyrrollidinylamide of Formula (IIIc)

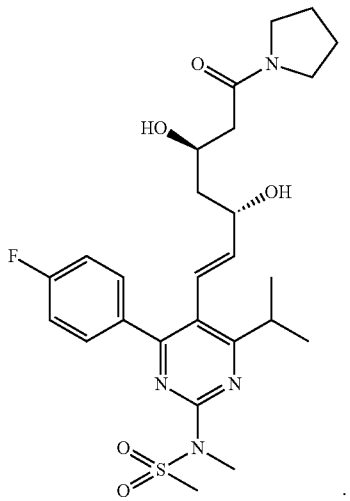

(IIIc)

6. The method according to claim 2, wherein in the compound of Formula (X), $R^1$ is 1-butyl or 2,2-dimethyl-ethyl and $R^2$ and $R^3$ are hydrogen.

7. The method according to claim 2, wherein for each mole of the compound of Formula (III) 1 to 30 molar equivalents of the compound of Formula (X) are reacted.

8. The method according to claim 2, wherein the reaction is carried out at a temperature between 80 and 140° C.

9. The method according to claim 1, which is the method II.

10. The method according to claim 9, wherein in the compound of Formula (X), $R^1$ is 2,2-dimethylethyl, and $R^2$ and $R^3$ are hydrogens.

11. The method according to claim 9, wherein in the compound of Formula (X), $R^1$ is 1-butyl, and $R^2$ and $R^3$ are hydrogens.

12. The method according to claim 9, wherein the rosuvastatin ammonium salt of Formula (II) is transformed into the rosuvastatin calcium salt of Formula (IV).

13. The method according to claim 1, which is the method III.

14. The method according to claim 13, wherein in the compound of Formula (X), $R^1$ is 2,2-dimethylethyl, and $R^2$ and $R^3$ are each hydrogens.

15. The method according to claim 13, wherein in the compound of Formula (X), $R^1$ is 1-butyl, and $R^2$ and $R^3$ are each hydrogens.

16. The method according to claim 1, which is the method IV.

17. The method according to claim 1, which is the method V.

18. A crystalline Form II rosuvastatin t-butylammonium salt of Formula (IIa)

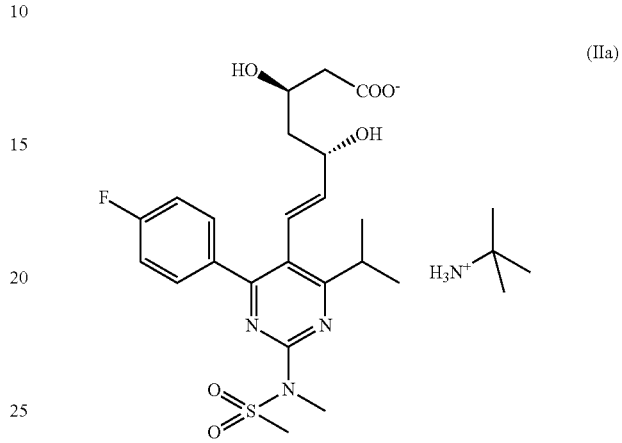

(IIa)

which has the following X-ray diffraction lines measured by CuKα radiation (±0.2° 2Θ): 18.654 degrees 2Θ; or 18.654 and 15.803 degrees 2Θ; or 11.282, 15.803 and 19.832 degrees 2Θ; or has the powder X-ray diffractogram of FIG. 1.

19. The crystalline Form II rosuvastatin t-butylammonium salt of Formula (IIa) according to claim 18, which has the following X-ray diffraction lines measured by CuKα radiation (±0.2° 2Θ): 18.654 and 15.803 degrees 2Θ.

20. The crystalline Form II rosuvastatin tert-butylammonium salt of Formula (IIa) according to claim 18, which has the following X-ray diffraction lines measured by CuKα radiation (±0.2° 2Θ): 11.282, 15.803 and 19.832 degrees 2Θ.

21. The crystalline Form II rosuvastatin t-butylammonium salt of Formula (IIa) according to claim 18, which has the following X-ray diffraction lines measured by CuKα radiation: (±0.2° 2Θ): 18.654 degrees 2Θ.

22. The crystalline Form II rosuvastatin t-butylammonium salt of Formula (IIa) according to claim 18, which has the powder X-ray diffractogram of FIG. 1.

* * * * *